(12) United States Patent
Kenten et al.

(10) Patent No.: US 8,450,066 B2
(45) Date of Patent: May 28, 2013

(54) METHODS FOR IDENTIFYING THE ACTIVITY OF GENE PRODUCTS

(75) Inventors: John H. Kenten, Boyds, MD (US); Douglas B. Woods, Gaithersburg, MD (US)

(73) Assignee: Meso Scale Technologies LLC, Gaithersburg, MD (US)

( * ) Notice: Subject to any disclaimer, the term of this patent is extended or adjusted under 35 U.S.C. 154(b) by 1955 days.

(21) Appl. No.: 10/726,069

(22) Filed: Dec. 3, 2003

(65) Prior Publication Data

US 2004/0137488 A1 Jul. 15, 2004

Related U.S. Application Data

(60) Provisional application No. 60/430,402, filed on Dec. 3, 2002.

(51) Int. Cl.
*C12Q 1/68* (2006.01)

(52) U.S. Cl.
CPC .................................. *C12Q 1/6897* (2013.01)
USPC .......... 435/6.13; 435/69.1; 435/458; 424/450

(58) Field of Classification Search
None
See application file for complete search history.

(56) References Cited

U.S. PATENT DOCUMENTS

| | | | |
|---|---|---|---|
| 5,728,533 A * | 3/1998 | Gallatin et al. | 435/7.1 |
| 5,908,705 A | 6/1999 | Nguyen et al. | |
| 5,942,399 A * | 8/1999 | Hillman et al. | 435/6 |
| 6,303,772 B1 | 10/2001 | Sherr et al. | |
| 6,383,733 B1 | 5/2002 | Beug et al. | |
| 2003/0028002 A1 | 2/2003 | Sherr et al. | |
| 2003/0077664 A1 | 4/2003 | Zhao et al. | |

OTHER PUBLICATIONS

Cheng et al. "Fluorescence in situ hybridization method for measuring transfection efficiency" BioTechniques 21:486-491 (1996).
El-Sankary et al. "Use of a reporter assay to predict and rank the potency and efficacy of CYP3A4 inducers" Drug Metabolism and Disposition 29:1499-1504 (2001).
Fejes-Tóth et al. "Subcellular localization of mineralocorticoid receptors in living cells: Effects of receptor agonists and antagonists" Proc. Natl. Acad. Sci. USA 95:2973-2978 (1998).
Grimm et al. "Robotic high-throughput assay for isolating apoptosis-inducing genes" BioTechniques 32:670-677 (2002).
Gupta et al. "Direct transcriptional activation of human caspase-1 by tumor suppressor p53" J. Biol. Chem. 276:10585-10588 (2001).
Horbinski et al. "Polyethyleneimine-mediated transfection of cultured postmitotic neurons from rat sympathetic ganglia and adult human retina" BMC Neurosci. 2:2 (8 pages) (2001).
Lim et al. "A simple assay for DNA transfection by incubation of the cells in culture dishes with substrates for beta-galactosidase" BioTechniques 7:576-579 (1989).
Reddy et al. "Tartrate-resistant acid phosphatase gene expression as a facile reporter gene for screening transfection efficiency in mammalian cell cultures" BioTechniques 15:444 and 447 (1993).
Yerushalmi et al. "Attenuating the growth of tumors by intratumoral administration of DNA encoding *Pseudomonas* exotoxin via cationic liposomes" Cancer Gene Therapy 7:91-96 (2000).
Werner et al. "Wild-type and mutant p53 differentially regulate transcription of the insulin-like growth factor I receptor gene" Proc. Natl. Acad. Sci. USA 93:8318-8323 (1996).

\* cited by examiner

*Primary Examiner* — Jim Ketter
(74) *Attorney, Agent, or Firm* — Nixon & Vanderhye PC

(57) ABSTRACT

The invention comprises compositions and methods for determining the function of proteins. It advantageously uses cotransfection of a reporter gene to remove transfection efficiency as a factor affecting the success of cell based assays. This method links the activity of the gene product of interest to the expression of the reporter gene. In addition, it also allows for the development of assays that allow for rapid screening for protein function in cells and whole animals by using cloned genes in a high throughput assay format which is simple, fast and inexpensive.

19 Claims, 2 Drawing Sheets

METHODS FOR IDENTIFYING THE ACTIVITY OF GENE PRODUCTS

CROSS-REFERENCE TO RELATED APPLICATION

This application claims priority to U.S. Provisional Application No. 60/430,402 filed Dec. 3, 2002, which is incorporated herein by reference.

FIELD OF THE INVENTION

This invention relates to cell-based methods of identifying gene products having an activity of interest. The invention includes methods of identifying proteins having pro-apoptotic or anti-apoptotic activities. Methods may be used to screen gene libraries for genes encoding gene products having the activity of interest. The methods may also be used to screen for drugs that modulate the activity of interest. The invention also includes cells, reagents, kits, systems and instrumentation for carrying out the methods of the invention.

BACKGROUND OF THE INVENTION

Now that the human genome has been sequenced, there has been a surge in interest in identifying the function of the proteins coded by the newly identified genes. A variety of in vitro biochemical approaches exist for studying protein function, e.g., methods for measuring enzymatic activities, methods for measuring binding interactions, etc. These methods generally require some advance knowledge of the types of activities that might be found, e.g., the structure of an enzymatic substrate or potential binding partner.

An alternative approach is to transfect a cell with a gene of interest and look for the ability of the gene to change a phenotype of the cell. The advantage of this cell-based approach is that it allows identification of proteins that are involved in a specific phenotype or cell behavior without knowing the biological pathways involved in that phenotype or cell behavior. A drawback of cell-based assays is that they tend to be laborious and not amenable to the high-throughput screening of genes. There is a need for improved high-throughput cell-based methods for identifying the function of proteins.

SUMMARY OF THE INVENTION

The invention comprises compositions and methods for determining the function of proteins and other gene products. It preferably uses cotransfection of a reporter gene. This method links the activity of the protein of interest to the expression of the reporter gene. In addition it also allows for the development of assays that allow for rapid screening for protein function in cells and whole animals by using cloned genes in a high throughput assay format which is simple, fast, and inexpensive.

The present invention provides an efficient method for determining if the gene product has an activity of interest. According to a preferred embodiment of the invention cells are co-transfected with two vectors, preferably with two vectors containing promoter sequence, preferably by treating cells with the first vector, second vector, and a transfection reagent, where the first vector contains a coding sequence for a gene product of interest and the second vector contains a reporter gene. Cells co-transfected with the test gene and reporter gene express both products. Preferably, the test gene is selected from a library of genes encoding at least two different proteins, more preferably from a library containing at least 1000 different genes. Co-transfection may be carried out for each member of the gene library, preferably in one or more multi-well plates, to screen for members having an activity of interest. The abundance and/or activity of the reporter gene product may be modulated by the presence of the test gene product and the abundance and/or activity of the reporter gene product are measured.

The determination if the test gene product has an activity of interest is made on the basis of the measured reporter gene product's abundance and/or activity. Preferably the activity is an enzymatic activity that catalyzes the reaction of a substrate to form a product. More preferably the activity is measured by adding substrate and measuring the substrate consumption, or product formation. In some specific embodiments of the present invention the activity of the reporter gene product is a β-galactosidase, β-lactamase, or luciferase activity. According to another preferred embodiment, a luminescent reporter protein is measured by inducing and measuring luminescence. According to yet according to another preferred embodiment, the reporter protein is measured through a binding assay or electrophoresis.

In another preferred embodiment of the present invention, the reporter gene product affects or regulates a biological process in the cell and the activity of the reporter protein is measured by observing one or more indicators of the state of the biological process, preferably by measuring a change in cell morphology, a change in abundance of a native protein, a change in post-translational modification (e.g., peptide cleavage, phosphorylation, conjugation of carbohydrate, peptide, or lipid) of a native protein, a change in transcription of a native gene, a change in translation of a native transcript, a change in processing or secretion of a native protein, a change in accumulation of insoluble protein deposits, or any other observable change in a cellular process.

In certain preferred embodiments of the invention, a negative control is carried out to establish the activity and/or abundance of the reporter product in the absence of a test protein with the activity of interest. Preferably, the negative control is carried out by repeating the co-transfection assay without the test vector and, optionally, replacing the test vector with i) a vector coding for a protein that is known to not have the activity of interest; ii) an empty vector (i.e., a vector that is analogous to the test vector except that it does not have a functional protein coding sequence) or iii) a vector that does not have a functional promoter. Comparison of the abundance and/or activity of the reporter product measured in the co-transfection assay with that measured in the negative control assay is used to determine if the test protein modulates the abundance and/or activity of the reporter product and, therefore, has the activity of interest. In screens of large numbers of test proteins, especially if the number of proteins with the activity of interest is expected to be low, the negative control can be replaced with a statistical representation of the test proteins with the lowest activity, e.g., the median or average test value obtained for a sampling of the test proteins with the lowest activity (e.g., in a sampling of the half of the proteins with the lowest activity).

Optionally, positive controls are also carried out. Preferably, the positive controls are carried out by repeating the co-transfection assay but replacing the test vector with an analogous vector that codes for a protein known to have the activity of interest. The relative activity of a test protein can be represented by relation to the activity of the negative and positive controls. For example, a useful indicator of the activity of a test protein is the ratio $(A_t-A_n)/(A_p-A_n)$, where $A_t$, $A_n$ and $A_p$ are, respectively, the activity and/or abundance of the reporter measured in the presence of the test vector, the negative control and the positive control.

The methods of the invention are readily scalable for high-throughput screening in multi-well plates. Preferably, transfection in high through-put applications is carried out by adding a transfection reagent to individual wells of one or more multi-well plates (more preferably, to wells that are coated with a polycation), followed by adding first and second vectors and then followed by adding cells and incubating the multi-well plate(s) to allow cells to incorporate the first and second vectors.

The present invention is also directed to a method for determining if a gene product has pro-apoptotic or anti-apoptotic activity by co-transfecting a test gene and a reporter gene in cells. Both gene products are expressed and the pro- or anti-apoptotic activity can be determined based on measuring the activity of a reporter gene product.

Yet according to another preferred embodiment of the present invention a secondary assay is conducted to confirm that transfection with the test protein results in a change in the level of an apoptosis marker, preferably an apoptosis marker selected from the group of caspase activation, annexin staining on the outer membrane, DNA ladder formation, and detection of the cleavage products of caspase such as DFF45, alpha fodrin, and lamin A, and preferably is repeated in a different cell line having a different genetic background than the initial cell line.

BRIEF DESCRIPTION OF THE DRAWINGS

The present invention is described with reference to the accompanying drawings wherein.

DETAILED DESCRIPTION OF THE INVENTION

Figure 1:
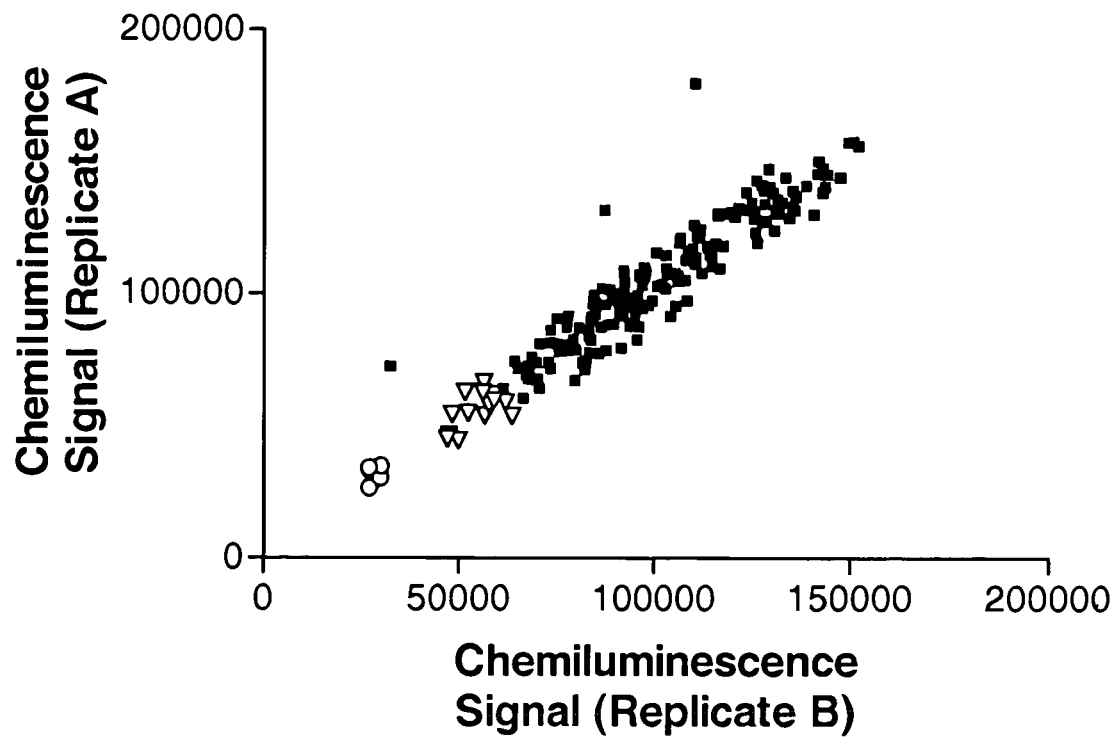
FIG. 1 shows the results of a screen of 200 cDNA clones for pro-apoptotic or anti-apoptotic genes. U2OS cells were co-transfected with a vector comprising a gene from a gene library and a vector comprising the gene for β-galactosidase. Each data point represents results for a specific member of the gene library. The X-axis and Y-axis represent the β-galactosidase activity measured when the experiment was run using DNA prepared at different times.

The invention includes methods for identifying gene products having an activity of interest. In particular, the invention provides methods involving transfecting a cell with a gene of interest and detecting changes in the phenotype of the cell, e.g., changes in cell viability, cell morphology, cell cycle, protein expression, mRNA transcription, etc. This invention provides an improved method for the detection and selection of genes that are involved in perturbing cell cycle, protein expression, cell death, and apoptosis. The method, preferably, uses a co-transfection technique to introduce both a gene of interest and a reporter gene into a cell.

In one embodiment of the present invention, the reporter gene is present as a control to determine the level and efficiency of the transfection. In another preferred embodiment, the reporter gene product is used to determine the status of the cell such as cell viability with respect to the cell cycle, protein expression, cell death, and/or apoptosis.

Yet in another embodiment, the activity and/or abundance of the reporter gene is modulated by an activity of the test gene of interest, thus allowing for the screening of test gene products for gene products having this activity and/or the measurement of this activity in selected gene products. For example, the reporter gene may be linked to a specific cis acting enhancer linked to a promoter to drive the expression of the reporter gene.

The methods of the present invention preferably use indirect detection where the test protein causes a change in overall viability, cell phenotype, perturbations of cell cycle, protein expression, cell death, and apoptosis and the change is reflected in the amount or activity of a reporter gene product. Indirect detection methods work surprisingly well, according to the specific embodiments of the present invention.

In another preferred embodiment specific biomarkers are used to determine the effect of the transfected gene of interest or the co-transfected reporter gene. Examples of specific markers include caspase activation, DNA ladder formation, the measurement of the expression of specific proteins, etc.

Yet another preferred embodiment employs a reporter vector that comprises i) a reporter gene that encodes a reporter gene product such as a protein and ii) a specific regulatory element (e.g., the consensus sequence for a transcription factor such as NFkB) that is, preferably, linked to a known cellular pathway. The specific regulatory element is, preferably, on the 5'side of the reporter gene sequence. A change in the amount or activity of the reporter gene product reflects direct interaction of the test gene product with the specific regulatory element sequence or, alternatively, the interaction of the test gene product with an upstream regulator of the specific regulatory element. Examples of specific regulatory elements that may be used include consensus sequences for known transcription factors such as nuclear factor of kB cells (NFkB) cis acting enhancer, nuclear factor of activated T-cells (NFAT) cis acting enhancer, CRE-binding protein (CREB) cis acting enhancer, cAMP response element (CRE) cis acting enhancer, serum response element (SRE) cis acting enhancer, or combinations thereof. In an especially preferred embodiment, the reporter gene codes for luciferase. By way of example, a reporter vector comprising a NFkB consensus sequence located 5' from a sequence coding for luciferase may be used to screen for proteins that bind to the consensus sequence or affect NFkB activation (e.g., proteins that play a role in, or otherwise affect, NFkB-linked inflammatory responses such as cell activation via TNF receptor, IL-1 receptor and Toll-like receptors). Co-transfection with a gene that codes for a protein that is an upstream activator of NFkB will lead to an increase in luciferase activity relative to cotransfection with a gene that codes for an inactive protein. Co-transfection with a gene that codes for a protein that is an upstream inhibitor of NFkB will lead to a decrease in luciferase activity.

The present invention provides an efficient method for determining if the gene product has an activity of interest. In one preferred embodiment, the gene of interest is cloned into a vector and co-transfected with a reporter gene also cloned into a vector, preferably a vector of the same vector type. Both the gene of interest and the reporter gene are taken up and expressed in the transfected cells. The activity of a reporter gene product may be modulated by the presence of a test gene product and the activity of a reporter gene product is measured. Preferably, following the trasfection, the genes are allowed to express (typically for 24-48 hours) and the cellular levels of the reporter gene product are determined using assays based on the detection of the enzymatic activity, the binding activity (ability to bind a specific binding partner such as a ligand, receptor, antibody, etc.) or an intrinsic physical property (e.g., an optical property such as fluorescence, chemiluminescence, bioluminescence, etc.) of the reporter. According to one especially preferred embodiment of the present invention, vectors and reporters are used that are relatively unaffected by cellular regulatory processes, cell type, etc. (e.g., vectors comprising non-specific promoters) so that the activity of the reporter in a transfected cell is, primarily, indicative of the viability of the cell. Most preferably, the CMV-SPORT6 vector and beta-galactosidase reporter may be used. The determination if the test gene product has an activity of interest is made on the basis of the measured reporter gene activity. In the case where the gene of interest retards cell growth, differentiation, or activates apoptosis, the detectable reporter levels should be lower. Therefore, in one specific embodiment of the present invention, the method allows for the selection of genes involved in apoptosis.

According to another preferred embodiment of the present invention, the method is readily scalable for high-throughput screening in multi-well plates or high-density arrays.

The present invention is also directed to a method for determining if a gene product has pro-apoptotic or anti-apoptotic activity by co-transfecting a test gene and a reporter gene in cells. Both gene products are expressed and the pro- or anti-apoptotic activity can be determined based on measuring the activity of a reporter gene product. This embodiment is also readily scalable for high-throughput screening.

Transfection is often a low efficiency process. As a result, a phenotype change usually occurs in a small percentage of cells and the effect triggered by the gene of interest may be hard to observe given high background of non-transfected cells. Surprisingly, in co-transfection experiments involving transfection with two vectors, while the efficiency of transfection may still be low, the probability that a transfected cell has the genes from both vectors is high. Co-transfection with the reporter according to the present invention insures that, for the most part, only cells having the gene of interest are interrogated. Selection for drug resistance and/or stably transfected cells are not required to initially determine the gene's function. The present invention also provides for cell sorting, such as with fluorescently or magnetically labeled antibody, therefore selectively enriching a subpopulation of cells having the gene of interest.

Vectors of the invention consist of a nucleic acid sequence that contains a sequence element such as an origin of replication that allows the vector to replicate in a host or in vitro. Examples of vectors that can be used in the subject invention as described above include, pCMVSPORT6, pCMVSPORT, pCMVSPORT2, pCMVSPORT4, pCMVSPORT6.ccdb, pCMVSPORT6.1.ccdb, pSVneo, pTracer-CMV, pIND, pGene/V5his, pcDNA family (Invitrogen, CA), pTet-On, pTet-Off, pTRE2, pIRES, pCMV-Myc, pCMV-neo, pPUR, pMSCVneo (Clontech, CA), pSI, pCI, and pTarget™ (Promega, WI).

According to the instant invention, the vector will, preferably, contain a functional promoter sequence that will initiate transcription in the desired cell. Non-specific promoter sequences, or promoter sequences specific for a tissue type, cell cycle or cell state, may be used with the methods of the present invention. Examples of promoters with low cell type selectivity include commonly used CMV IE and SV40 early viral promoters and examples of promoters driving the constitutive expression of normal endogenous genes including beta actin (class II) and U6 (class III) promoters. Examples of a tissue, cycle or state specific promoters include promoters containing NFkB enhancer elements (state specific), cyclin E promoter (cell cycle specific), topoisomerase IIalpha (topo IIalpha) promoter, which is activated during the late S and G(2)/M phases of the cell cycle, CaMKII promoter (tissue specific), adipocyte specific promoter ap2, and PSP94 gene promoter/enhancer for prostate tissue-specific expression. The specific promoters may be used to improve selectivity by limiting the measured response to a given cell type, cell cycle or cell state respectively.

According to another preferred embodiment of the present invention, a promoter is under the control of a small molecule, which allows for fine tuning the temporal expression profile and therefore allows an increase in the selectivity of the response by selecting an optimal time for expression analysis. Examples include the Tet-On™ and the Tet-Off™ systems (Clontech, CA) where the expression can be turned on or off by the addition of tetracycline. Other vector systems that may be used in the methods of the present invention to control gene expression in a similar fashion include the GeneSwitch™ system induced by mifepristone and the ecdysone-inducible system induced by ecdysone, ponasterone A, and muristerone A (Invitrogen, CA).

Tetracycline-regulated gene expression systems have been widely used to allow temporal and quantitative control of transgene expression in cultured cells and transgenic animals.

According to one embodiment of the invention, the vector may also contain a sequence element that will direct the addition of a polyA sequence to the RNA transcribed from the promoter. Examples of this element include the SV40, HSV TK, growth hormone, and beta globin poly A sequence elements. According to another embodiment of the invention, the vector may also contain viral sequences involved in packaging nucleic acid into viral particles to allow facile delivery of DNA. Examples of these sequences include the retroviral packaging sequences described in U.S. Pat. Nos. 5,512,421, 5,670,354, and 5,766,945 (which are incorporated by reference herein) and the adenoviral sequences.

The transfection technology utilizes numerous formulations and methods. The transfection methods are preferably chosen from one of the following categories: (i) chemical (e.g., lipofection and calcium phosphate), (ii) physical (e.g., electroporation and ballistic transfection techniques such as the "gene gun"), and (iii) viral (e.g., using viral vectors such as adenoviruses and retroviruses). Another suitable transfection technique is protoplast fusion. One embodiment involves the use of lipids (preferably cationic lipids) mixed with targeting moieties (or alternatively, comprising modified lipids that are linked to targeting moieties) where the targeting moieties are moieties that enhance transport of species (e.g., species linked or complexed to the targeting moiety) through the plasma or nuclear membranes. A variety of peptides and proteins are known in the art for this property including the charged sequence for SV40 T antigen having the sequence PKKKRKV (SEQ ID NO:1) and its well known variations for nuclear localization. Lipid preparations that have proteins that facilitate retrograde transport using endosomal mechanisms would be similarly useful in increasing transfection efficiency. The transfection methods include methods that lead to transient transfection and stable transfection. Stable expression is used to establish stable cell lines: vector DNA integrates into a small % of cells and these are selected for survival by growing cells on antibiotic containing media. This method is usually 10- to 100-fold less efficient. All categories and classes may be used with the methods of the present invention. However, transient lipofection worked surprisingly well in some preferred embodiment of the present invention and proved especially advantageous in allowing the methods of the invention to be carried out in a high-throughput, multi-well plate format. We have found that co-transfection using transient lipofection, according to the methods of the invention, produces a high efficiency of co-transfection (that is, when a cell is transfected it is highly likely that it contains both genes).

The present invention provides preferred chemical methods for HTS applications which use a formulation that includes lipids (preferably a cationic lipid) and other reagents that form complexes with the vector nucleic acid in such a way that on contact with cells the DNA is taken up by the cells. The preferred examples of these reagents are proprietary lipid compositions like DMIRE-C, cellFECTIN®, Lipofectin®, oligofectAMINE™, lipofectAMINE™, lipofectAMINE PLUS™, lipofectAMINE 2000™ (Invitrogen, CA), fugene (Roche, IN), Effectene (Qiagen, MD), TransFast™, Tfx™, Transfectam® (Promega, WI), siPORT™ amine, siPORT™ lipid (Ambion, TX), and GeneJuice (Novagen, CA). Preferably, transfections are carried out by combining the transfection reagent, vectors, and cells in a container, most preferably the well of a multi-well plate. Preferably, the well is coated with a polycationic polymer and, most preferably, poly-lysine. The components of the transfection reaction may be added in different orders, however, it is preferred to combine the vectors and transfection reagent and then add the cells. In addition to the preferred reagents of the present invention, other reagents maybe used to achieve the same result. These reagents include DEAE dextran and calcium phosphate. Chemical transfection methods are surprisingly simple, reproducible, relatively efficient, and could be adapted for screening large gene libraries.

Alternatively, the vector nucleic acid may be packaged into viral coats to allow the uptake of the genes of interest. Examples of this method include retroviral packaging methods such as described in U.S. Pat. Nos. 5,512,421, 5,670,354, and 5,766,945 (which are incorporated by reference herein), and the adenovirus packaging system (Clontech, CA). These viral based systems are good choices for high-throughput screening applications, although the process of the viral packaged nucleic acid generation can be complex and expensive.

Any transcription technique which introduces nucleic acid into cells where DNA is transcribed and RNA is translated can be used with the methods of the present invention. The methods are suitable for the generation of stable cell lines when used in combination with a vector that contains a selectable marker gene such as Puro, Hyg, Zeo Bsd, or Neo (Invitrogen and Clontech). Selectable marker genes provide the means for the selection of the few cells that ultimately integrate the DNA into the genome. But selection for stably transfected cells is not required to make the initial determination of identifying the activity of a gene of interest.

The transfection may be detected via the expression of a reporter gene product, or via change in cellular phenotype or vitality. The cells may be selected based on incorporation of the antibiotic resistance genes used as selectable elements by co-transfecting them with the gene of interest. After selecting for antibiotic resistance for a period of time, only cells that express the selectable marker and a gene of interest are left. Therefore, the results of the gene of interest overexpression on cell phenotype or a selected biological process may be assessed. This method is preferentially used with stable transfection.

More preferably, reporter genes coding for reporters having measurable activities (e.g., β-galactosidase or enhanced green fluorescent protein (eGFP)) may be used as convenient indicators. In this case, the expression of the reporters may be measured by measuring an activity of the reporter such as luminescence, enzyme activity, binding activity, etc. This measurement may be carried out on whole cells or may involve lysing the cells to release the reporters from the cells. A reporter gene can be used to indicate both where it is expressed and how strongly it is expressed. The activity of the reporter gene product can be measured quantitatively and is used preferentially in transient transfection assays. Alternately, mRNA transcripts derived from reporter genes may be measured instead of the protein products coded by the genes.

According to a preferred embodiment of the present invention, the reporter genes can be used both to measure the efficiency of transfection (as controls of transfection) and to 'report' the activity of a gene of interest when the cell state responds to different experimental conditions.

The preferred reporters of the invention include beta-galactosidase, beta-lactamase, fire fly luciferase, renilla luciferase, bacterial luciferases, RNA sequences transcribed from the co-transfected vector, proteins containing epitope tags such as flag and/or myc and/or V5 (Invitrogen), and GFP and its derivatives.

In the case of beta-galactosidase, one preferred activity assay method is to make use of a substrate, such as a stabilized dioxetane substrate (e.g., the dioxetane substrates developed and sold by Tropix) that generates a luminescent product. This method takes advantage of the amplification inherent in enzymatic assays as well as the high sensitivity of chemiluminescence measurements. Beta-galactosidase can alternatively be detected using calorimetric, or fluorescent methods were the substrate generates a colored or fluorescent product respectively on the hydrolysis of the beta-galactosidase bond that is then detected spectophotometrically. For example, a β-gal hydrolysis of the artificial substrate ONPG creates a yellow product, or if cells that express β-gal are exposed to the artificial substrate X-gal, it is cleaved to an insoluble blue product that is visible within the cell.

Luciferases such as those from firefly and renilla are detected using the native substrates for these enzymes (e.g., luciferin) when the light is generated due to enzymatic substrate activation. The reagents for these assays are available from numerous sources such as Roche and Promega. Using the chemiluminescent substrates for beta-galactosidase and the natural substrates for the luciferases generally provides better sensitivity for the detection of these reporters.

In certain preferred embodiments of the invention, the reporter gene comprises the sequences of one or more affinity tags so that the gene product comprises one or more affinity tags. Affinity tags (also sometimes referred to as epitope tags) are peptide sequences that are introduced into recombinant proteins because of their known ability to specifically bind a binding partner. The affinity tags can then be used for immobilizing or purifying the recombinant protein via the specific binding interaction. Alternatively, the affinity tag may be used to measure the reporter via a specific binding interaction, e.g., by using a labeled binding partner of the affinity tag. Examples of affinity tags that are known in the art include epitopes with known antibody binding partners such as myc and flag, peptides with affinity for metal ions such as oligo histidine sequences (e.g., $His_6$), receptors known to bind specific ligands (e.g., GST) and modification sites that are modified in vivo with haptens or ligands (e.g., known sites of biotinylation).

In one preferred embodiment of the invention, the reporter comprises at least one affinity tag. This affinity tag is used to purify, immobilize and/or detect the reporter prior to measuring the amount and/or activity of the reporter. In one class of preferred assays, the reporter (or a similar substance) is naturally present in a cell line. By co-transfecting with a reporter comprising an affinity tag, it is possible to measure the activity of the expressed reporter without interference from the endogenous reporter-like substances. The affinity tag is also advantageous when it is necessary to purify the reporter prior to measuring its activity. For example, the reporter may be captured on a surface (e.g., via a specific binding interaction with an immobilized binding partner of the affinity label), optionally purified by washing the surface so as to remove reporter-like substance, and then detected (e.g., via its enzymatic activity, luminescence properties and/or its ability to bind a second binding partner directed to the reporter, the second binding partner preferably being labeled with a detectable label), preferably via a surface selective technique such as electrochemiluminescence detection of an electrochemiluminescent label. Alternatively, the reporter is captured on a surface using an immobilized binding partner of the reporter and is detected using a, preferably labeled, binding partner of the affinity label.

In one preferred embodiment, an assay is conducted to measure the ability of a test gene product to influence the post-translational modification of a reporter. A cell is co-transfected with a vector coding for the test gene product and a vector coding for a fusion protein comprising the reporter and an affinity tag. After allowing the proteins to express, the fusion protein is captured on a surface via a binding partner of the affinity tag and detected using a binding reagent that is specific for the post-translational modification and that is, preferably, labeled with a detectable label. The amount of post-translationally modified reporter is then measured and, preferably, is compared to a control cell that was not transfected with the test gene. In an alternative embodiment, the binding reagent that is specific for the post-translational modification is immobilized on the surface and used for capture and the binding partner of the affinity tag is used for detection. Assays as described above may be used to measure the influence of a test gene product on the phosphorylation, dephosphorylation, proteolytic cleavage, ubiquitinylation, deubiquitinylation, Neddylation, glycosylation, modification with fatty acid groups, etc. of a reporter protein.

In another embodiment of the invention, a fusion protein comprising a first affinity tag and a second affinity tag is used as a reporter protein. The amount of the affinity tag is measured using a sandwich binding assay that employs a first binding partner specific for the first affinity tag and a second binding partner specific for the second affinity tag. Preferably, one of the binding partners is immobilized on a surface and the other is labeled with a detectable label to allow the assay to be carried out in a solid phase sandwich binding assay format. The reporter gene may be in a vector that is relatively unaffected by cellular regulatory processes, cell type, etc. (e.g., vectors comprising non-specific promoters) so that the activity of the reporter in a transfected cell is, primarily, indicative of the viability of the cell. Alternatively, the vector comprising the reporter gene may have a promoter or other regulatory sequence that is strongly coupled to an activity of interest so as to allow for the measurement of the activity of interest.

The methods described above may be used to screen for apoptosis inducing genes by co-transfecting the genes of interest and a reporter gene into selected cell lines. According to one preferred embodiment of the present invention, the transfected cells are allowed to take up the DNA and express the proteins from both the gene of interest and the reporter gene for 24-48 hours. Following the incubation, the culture medium is removed from the cells and the cells are lysed. The released reporter then may be detected quantitatively. Preferably, the vector and reporter are chosen so as to be relatively unaffected by cellular regulator processes, cell type, etc. (e.g., vectors comprising non-specific promoters) so that the activity of the reporter in a transfected cell is, primarily, indicative of the viability of the cell. Using the signal levels generated by the assay for the reporter, the genes of interest are segregated into those having no measurable effect and those with signals that are measurably lower that the control gene that has no apoptotic activity. The genes of interest that resulted in the lower signals represent a pool of genes that is now enriched in genes that cause apoptosis. This pool is then subjected to secondary screening methods that identify the apoptotic genes from the pool of the apoptotic candidate genes. Additionally, many cell lines have a baseline level of apoptosis, screening for test genes that generate signals higher than the controls may be used to screen for proteins that have anti-apoptotic effects. The preferred method of the present invention may be readily adapted for a high-throughput screening using modern automation in liquid handling and detection.

The present invention also provides for secondary screens to confirm the activity of primary screening hits and their role within a correspondent biological pathway. In one preferred embodiment, the invention is directed to detecting and verifying the activity of gene products involved in apoptosis.

According to one embodiment of the present invention, a number of classical markers can be used to determine if a transfected gene is activating a biological pathway, such as an apoptotic pathway. The apoptosis indicators include caspase activation, annexin staining on the outer membrane, DNA ladder formation, and detection of the cleavage products of caspase such as DFF45, alpha fodrin, and lamin A.

Furthermore, in order to determine if the hits from the screen are indeed targeting a general biological pathway and/or have activity in a broad range of cell types, the initial hits can be tested in one or more alternative cell lines. The approach allows filtering down to the set of genes that are key elements in the biological pathways. Preferably, in screens for apoptotic proteins, the proteins are screened in two cell types that differ in their sensitivity to apoptosis to allow for differentiation of pro-apoptotic genes into strongly pro-apoptotic genes and moderately pro-apoptotic genes. In another example, proteins are screened for an anti-tumor activity in a variety of tumor cell types or lines. Comparison of the activity in each of the cell types or lines allows for determining if the protein has anti-tumor effects in a cell lines or, e.g., if it is only active in tumors from certain tissues or having certain specific mutations.

The present invention also provides for drug screens for compounds that modulate an activity of interest. Preferably, the methods of the invention are used to screen gene libraries for gene products having an activity of interest. The gene products having this activity are then screened against a library of substances to find substances that modulate this activity. The scalability and reproducibility of the transfection and detection methods of the invention make it highly advantageous in screening large numbers of genes in gene libraries and make the same methodology easily adaptable to screening large numbers of compounds against selected members of gene libraries with activities of interest. Drug screens using the methods of the invention involve the additional step of incubating the transfected cells with potential drugs. This contacting may occur during the transfection step, during the expression of the transfected proteins or during a subsequent incubation of the transfected cell line.

EXAMPLES

The following examples are illustrative of some of the methods falling within the scope of the present invention. They are, of course, not to be considered in any way limitative of the invention. Numerous changes and modifications can be made with respect to the invention by one of ordinary skill in the art without undue experimentation.

Example 1

Screening Assay for Proteins Having Anti-Apoptotic or Pro-Apoptotic Activity

Approximately 200 individual cDNA clones coding for human or mouse proteins were purchased from Incyte Genomics. The genes were provided in the pCMV-Sport6 vector, a well-established vector that contains a 5'-CMV promoter sequence and a 3'-polyadenylation signal. cDNA clone (Gen Bank ID AW072826), which contained the gene sequence for the human BAX protein, was purchased from ATCC. The entire open reading frame for a bacterial β-galactosidase (β-gal) gene was also obtained in the pCMV-Sport6 vector (Invitrogen). The vectors were replicated and purified as necessary using established procedures.

The double transfection experiments were carried out using U2OS cells (a human osteosarcoma cell line, American Type Culture Collection Number HTB-96) or HEK-293 cells (a human embryonic kidney cell line, American Type Culture Collection Number CRL-1573). The cells were maintained by growth in cell culture flasks in DMEM containing penicillin, streptomycin and 10% fetal calf serum (FCS). These adherent cell lines were removed from the walls of the culture flasks with 0.25% trypsin, pelleted, and resuspended in DMEM containing 10% FCS prior to use.

The cells were co-transfected with the β-gal gene and a member of the gene library using the following procedure. A well of a white poly-lysine coated 96-well polystyrene tissue culture plate was treated with 40 uL of a solution containing 1 uL of Fugene-6 Transfection Reagent (Roche Biochemicals) in Dulbecco's Minimal Essential Media (DMEM). To this solution was added roughly 50-300 ng of a gene library clone in 0.75 uL of water followed by 125 ng of the β-gal clone in 20 uL of DMEM. The cells ($1\times10^4$ cells in 100 uL of DMEM containing 10% fetal calf serum) were added and the plates were allowed to incubate at 37° C. in a humidified atmosphere containing 5% $CO_2$. The supernatant was aspirated from the wells leaving the cells on the well bottom. The cells were lysed by adding 30 uL of cell lysis buffer (Galactostar kit, Perkin Elmer) and incubating for 5 min at room temperature. The cell lysate was combined with 60 uL of a chemiluminescent β-gal substrate (Galactostar, Perkin Elmer), the plate was shaken and incubated for 2 hours at room temperature, and the chemiluminescence intensity measured using a Spectramax luminescence reader.

FIG. 1 shows a comparison of assay results generated from U2OS cells using vectors that were expanded and purified on different days. The figure shows an excellent correlation between the two experiments. The figure also shows that some pro-apoptotic genes in the library were able to produce reductions in signals of greater than 3 standard deviations from negative controls (open triangles) or greater than 4 standard deviations from negative controls (open diamonds), the negative control signal being the average value measured in wells treated with an empty pCMV-Sport6 vector instead of a test gene. The result demonstrates the ability of the assay to sensitively identify pro-apoptotic genes. The assay was able to identify known pro-apoptotic genes: the BAX, Caspase 4, and TNFRSF10a (TNF receptor super family 10a) clones all gave signals that were more than 3 standard deviations lower than the controls. The strong reduction in β-gal signal in the presence of the BAX gene (>75% relative to the controls) shows that a large fraction (>75%) of the cells that were transfected with β-gal were also transfected with BAX in the co-transfection experiment.

Figure 2:
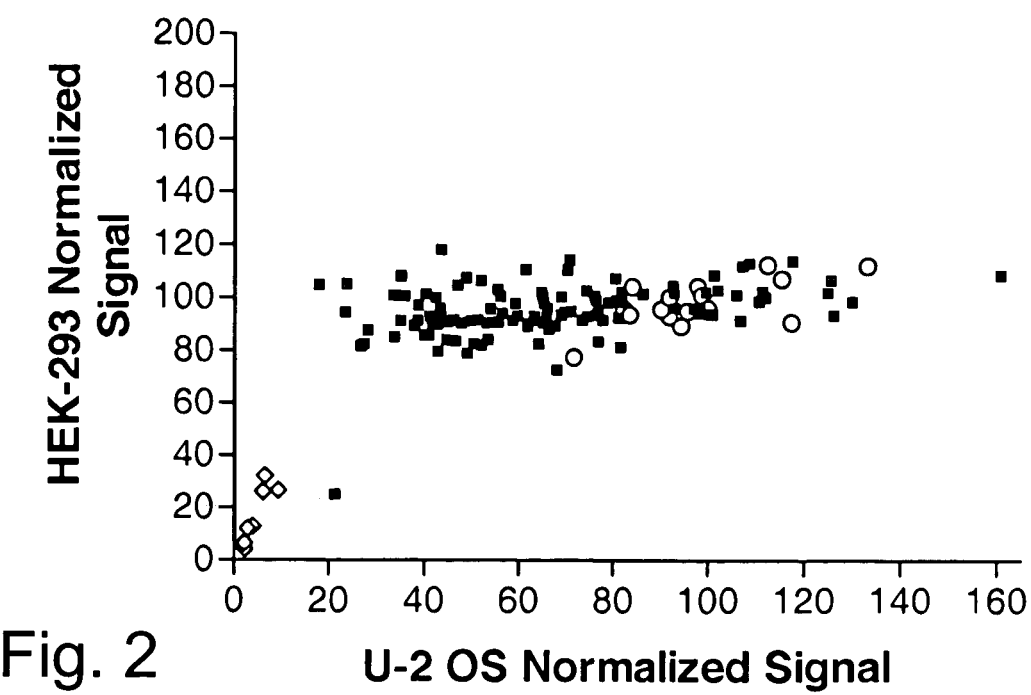
FIG. 2 shows the results of a screen of cDNA clones for pro-apoptotic or anti-apoptotic genes. Cells were co-transfected with a vector comprising a gene from a gene library and a vector comprising the gene for β-galactosidase. Each data point represents results for a specific member of the gene library. The figure compares the effect of the genes on two different cell lines (HEK-293 and U2OS).

FIG. 2 shows a comparison of the effect of a set of cDNA clones on U2OS cells and HEK-293 cells (the test genes are represented with closed squares, empty vectors having no test protein are represented with open circles and vectors containing sequences of the strongly pro-apoptotic gene Bax or analogs are represented with open diamonds). The figure shows that the strongest pro-apoptotic genes are picked up as strong positives with both cell lines demonstrating the use of parallel assays carried out using two cell lines to confirm hits. Interestingly, the U2OS cells appear to be much more sensitive to weak modulators of apoptosis. Presumably, the HEK-293 tumor line is strongly biased against apoptosis (this was expected based on the presence of adenoviral genes involved in blocking certain apoptotic pathways, 293 HEK cells are transformed by Ad5 E1 region) and requires a strong pro-apoptotic signal to initiate apoptosis. Because of its sensitivity, the U2OS cell line has proved to be especially useful in screens for modulators of apoptosis.

Figure 3:
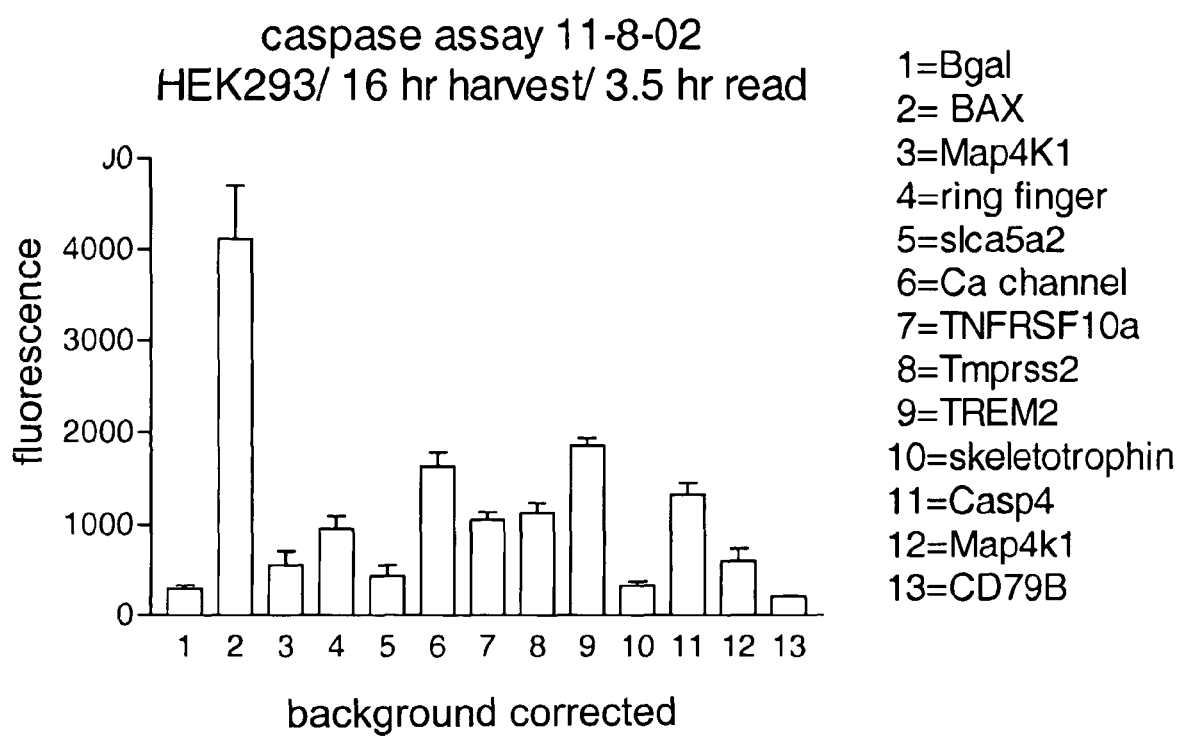
FIG. 3 shows the results of the secondary screen of the selected genes from the co-transfection based screen (FIG. 1) demonstrating the enrichment of the gene involved in apoptosis by this method. The assay shown is a Caspase 3/7 assay demonstrating the activation of a specific apoptotic pathway by the majority of the genes from the pool of selected genes. This assay was performed using HEK-293 cells.

A subset of the strongest apoptosis promoters identified by the screen were transfected into 293 cells and tested for caspase 3 or 7 activity, a marker for apoptosis, using a commercial kit (Promega). FIG. 3 shows that all of the clones except one produced caspase activity that was higher than the negative control cells confirming the pro-apoptotic effect of the genes. We hypothesize that the clone that produced lower caspase activity either signaled for a non-caspase dependent apoptotic pathway or initiated a non-apoptotic pathway of cell death.

The terms and expressions which have been employed are used as terms of description and not of limitations, and there is no intention in the use of such terms or expressions of excluding any equivalents of the features shown and described as portions thereof, its being recognized that various modifications are possible within the scope of the invention.

The invention claimed is:

1. A method for determining whether a gene product has an activity of interest comprising:
   (a) treating a well of a mufti-well plate with a transfection reagent comprising a cationic lipid preparation, wherein said well includes a coating comprising a polycationic polymer;
   (b) adding to said well (i) a first cell preparation, (ii) a first vector selected from a library of vectors, at least two members of said library comprising genes which encode different test proteins, and (iii) a second vector comprising a gene which encodes a reporter protein, wherein said reporter protein affects or regulates a biological process in said cell;
   (c) incubating the mufti-well plate to allow cells to incorporate the first and the second vectors;
   (d) expressing said different test proteins and said reporter protein in a transfected cell;
   (e) measuring abundance and/or activity of said reporter protein by observation of an indicator of said biological process in said transfected cell, wherein said abundance and/or activity of said reporter protein is modulated by the presence of a protein that modulates said reporter protein;
   (f) screening said library for one or more members which encode test proteins that modulate said reporter protein; and
   (g) repeating (a) to (e) in an additional well of said mufti-well plate with a further cell preparation having the same or different genetic background as said first cell preparation.

2. The method of claim 1, wherein said library comprises at least 1000 different genes.

3. The method of claim 1, wherein said transfection reagent further comprises a targeting moiety.

4. The method of claim 1, wherein said first vector and/or said second vector further comprise promoter sequences.

5. The method of claim 1, wherein said transfection reagent comprises at least one lipid composition selected from the group consisting of:
   (i) a liposome formulation of N,N',N'',N'''-tetramethyl-N, N',N'',N'''-tetrapalmitoylspermine (TM-TPS) and dioleoyl phosphatidylethanolamine (DOPE) in 1:1.5 (M/M) respectively,
   (ii) a liposome formulation of N-[1-(2,3-dioleyloxy)propyl]-N,N,N-trimethylammonium chloride (DOTMA) and dioleoyl phophotidylethanolamine (DOPE) in 1:1 (w/w) ratio respectively,
   (iii) a liposome formulation of 2,3-dioleyloxy-N-[2(sperminecarboxamido)ethyl]-N,N-dimethyl-1-propanaminium trifluoroacetate (DOSPA) and dioleoyl phosphatidylethanolamine (DOPE) in 3:1 (w/w) ratio respectively,
   (iv) a mixture of (+)-N,N[bis(2-hydroxyethyl)]-N-methyl-N-[2,3-di(tetradecanoyloxy)propyl] ammonium iodide and L-dioleoyl phosphatidylethanolamine (DOPE),
   (v) a mixture of [N,N,N',N'-tetramethyl-N,N'-bis(2-hydroxyethyl)-2,3-di(oleoyloxy)-1,4-butanediammonium iodide] and L-dioleoyl phosphatidylethanolamine (DOPE), and
   (vi) dioctadecylamidoglycyl spermine (DOGS).

6. The method of claim 1, wherein step (b) comprises:
   (i) adding said first vector, said second vector, and said transfection agent to said well; and
   (ii) adding said first cell preparation to the mixture formed in step (b)(i).

7. The method of claim 1, wherein abundance of said reporter protein is measured.

8. The method of claim 1, wherein said reporter protein is measured by luminescence.

9. The method of claim 1, wherein said reporter protein is measured by a binding assay for said reporter protein.

10. The method of claim 1, wherein said reporter protein is measured by electrophoretic analysis.

11. The method of claim 1, wherein said activity of said reporter protein is an enzymatic activity that catalyzes the reaction of a substrate to form a product, and said enzymatic activity is measured by adding said substrate and measuring consumption of said substrate and/or formation of said product.

12. The method of claim 11, wherein said enzyme activity is selected from the group consisting of β-galactosidase activity, β-lactamase activity, and luciferase activity.

13. The method of claim 1, wherein said indicator is selected from the group consisting of change is cell morphology, change in abundance of a native protein, change in post-translational modification of a native protein, change in transcription of a native gene, and change in secretion of a native protein.

14. The method of claim 1, wherein said activity of said reporter protein is aggregation and said reporter protein is Sup35.

15. The method of claim 1, wherein said activity of interest is pro-apoptotic or anti-apoptotic activity.

16. The method of claim 15 further comprising confirming that expression of said test protein results in a change in an indicator of apoptosis by another assay.

17. The method of claim 15, wherein said indicator of apoptosis is selected from the group consisting of DNA fragmentation, caspase activation, annexin staining on the outer membrane, DNA ladder formation, and production of cleavage products of caspase.

18. The method of claim 15, wherein said indicator of apoptosis is selected from the group consisting of DFF45, alpha fodrin, and lamin A.

19. The method of claim 1 wherein said repeating step (g) comprises repeating steps (a) to (e) in said additional well using a third vector instead of said first vector, said third vector differing from said first vector in that it: (i) does not code for a protein; (ii) codes for a protein that is known to not have the activity of interest; or (iii) does not have a promoter sequence; and said method further comprises:
   (h) comparing the activity and/or abundance of the reporter protein measured with said first vector and said third vector to determine whether said test protein has said activity of interest.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:

```
<223> OTHER INFORMATION: Description of Artificial Sequence: targeting
      peptide

<400> SEQUENCE: 1

Pro Lys Lys Lys Arg Lys Val
1               5
```